United States Patent
Ture et al.

(10) Patent No.: US 10,648,896 B2
(45) Date of Patent: May 12, 2020

(54) MODULAR PACKAGING SYSTEM FOR A LUBRICANT CONDITION MONITOR

(71) Applicant: Sikorsky Aircraft Corporation, Stratford, CT (US)

(72) Inventors: Cody Michael Ture, Fairport, NY (US); Christopher M. Minnella, Pittsford, NY (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 211 days.

(21) Appl. No.: 15/525,754

(22) PCT Filed: Sep. 11, 2015

(86) PCT No.: PCT/US2015/049672
§ 371 (c)(1),
(2) Date: May 10, 2017

(87) PCT Pub. No.: WO2016/076945
PCT Pub. Date: May 19, 2016

(65) Prior Publication Data
US 2017/0363529 A1    Dec. 21, 2017

Related U.S. Application Data

(60) Provisional application No. 62/078,652, filed on Nov. 12, 2014.

(51) Int. Cl.
*G01N 15/06* (2006.01)
*G01N 33/28* (2006.01)
(Continued)

(52) U.S. Cl.
CPC ..... *G01N 15/0656* (2013.01); *G01N 33/2858* (2013.01); *G01N 33/2888* (2013.01);
(Continued)

(58) Field of Classification Search
CPC .................................................. G01N 15/0656
(Continued)

(56) References Cited

U.S. PATENT DOCUMENTS

| 5,194,910 A |   | 3/1993 | Kirkpatrick, Jr. et al. |
|---|---|---|---|
| 5,706,783 A | * | 1/1998 | Sawada ................. F02B 61/045 |
|   |   |   | 123/406.47 |

(Continued)

FOREIGN PATENT DOCUMENTS

| WO | 2001037734 A1 | 5/2001 |
|---|---|---|
| WO | 2014123740 A1 | 8/2014 |
| WO | 2014138432 A1 | 9/2014 |

OTHER PUBLICATIONS

Notification of Transmittal of the International Search Report for International Application No. PCT/US15/49672 dated Feb. 22, 2016; dated Mar. 11, 2016; 10 pages.
(Continued)

*Primary Examiner* — John Fitzgerald
*Assistant Examiner* — Rodney T Frank
(74) *Attorney, Agent, or Firm* — Cantor Colburn LLP

(57) ABSTRACT

An apparatus for assessment of a fluid system includes a scaffold housing with a plurality of internal cavities; a debris monitor module assembly to be selectively inserted into a first cavity of the plurality of internal cavities, the debris monitor module assembly to determine wear debris information in a lubricant; a lubricant condition monitor module assembly to be selectively inserted into a second cavity of the plurality of internal cavities, the lubricant condition monitor module assembly to determine lubricant condition information in the lubricant; and a processing module assembly that is configured to be selectively inserted into a third cavity of the plurality of internal cavities, the processing module assembly to provide communication to an exter-
(Continued)

nal interface of at least one of the wear debris information and the lubricant condition information.

16 Claims, 5 Drawing Sheets

(51) Int. Cl.
  *G01N 15/10* (2006.01)
  *G01N 15/14* (2006.01)
(52) U.S. Cl.
  CPC ............... *G01N 2015/1062* (2013.01); *G01N 2015/1486* (2013.01)
(58) Field of Classification Search
  USPC ...................................................... 73/53.07
  See application file for complete search history.

(56) References Cited

U.S. PATENT DOCUMENTS

| | | |
|---|---|---|
| 7,239,155 B2 | 7/2007 | Byington et al. |
| 7,504,835 B2 | 3/2009 | Byington et al. |
| 2010/0270242 A1 | 10/2010 | Paradise |
| 2012/0025529 A1 | 2/2012 | Davis et al. |
| 2014/0144216 A1 | 5/2014 | Zhe et al. |

OTHER PUBLICATIONS

Written Opinion of the International Searching Authority for International Application No. PCT/US15/49672 dated Feb. 22, 2016; dated Mar. 11, 2016; 5 pages.

\* cited by examiner

MODULAR PACKAGING SYSTEM FOR A LUBRICANT CONDITION MONITOR

CROSS REFERENCE TO RELATED APPLICATIONS

This application is a National Stage application of PCT/US2015/049672, filed Sep. 11, 2015, which claims the benefit of U.S. Provisional Application No. 62/078,652, filed Nov. 12, 2014, both of which are incorporated by reference in their entirety herein.

STATEMENT REGARDING FEDERALLY SPONSORED RESEARCH OR DEVELOPMENT

This invention was made with Government support with the United States Army under Contract No. W911W6-10-2-0007. The Government therefore has certain rights in this invention.

BACKGROUND

The subject matter disclosed herein relates generally to the field of fluid analysis and, more particularly, to a modular packaging system for mounting sensor modules within an integrated lubricant quality assessment and debris monitoring device.

DESCRIPTION OF RELATED ART

Aircraft mechanical components require wear protection fluids, for example, fluids such as drive train lubricants and engine oils to keep the aircraft's components operating in an efficient and safe manner. Lubricating fluids can become degraded or contaminated by internal or external sources or accumulate component wear debris due to pitting, spalling, corrosion-induced fatigue, or other mechanisms. Further, water infiltration or chemical changes can degrade the lubricant and can affect oil-wetted component lifetimes and maintenance requirements.

Lubricant monitoring is being widely used for diagnostic and prognostic assessment of the health of mechanical components. Two typical lubricant monitoring techniques include lubricant analysis and detection of metallic debris suspended in lubricant flow. Lubricant analysis is typically performed off-line and may include lab analysis and optical inspection with a sample of lubricant from the system whose condition is to be assessed. The off-line lubricant analysis can be slow, labor intensive, expensive and error prone. On-line metallic debris monitoring may include a chip detector (magnetic plug) to collect ferrous materials for analysis and inspection. However, this metallic debris monitoring is not sensitive to detecting non-ferrous debris such as magnesium alloy or aluminum alloy. Typically, these two monitoring techniques are most commonly performed separately as they involve different technologies and processes.

Increasing reliance on condition based maintenance practices for aerospace powertrain systems, for example, debris detection and lubricant condition monitoring, demands integration of various sensor technologies to the greatest extent possible. This integrated package assembly, made up of various separate sensor assemblies, is typically operated in harsh environments. As a result, there exists a significant risk for failure of a single electrical component in a sensor assembly that can render the entire package assembly non-functional. Furthermore, the mechanical packaging needed to interface with these aircraft systems often requires the precision manufacture of exotic materials, substantially inflating the cost and lead time associated with upgrading core sensing capability. A packaging system that integrates lubrication condition monitoring with wear debris detection with sensor modules that can be serviced or replaced independently of other sensor modules is desired.

BRIEF SUMMARY

According to an aspect of the invention, an apparatus for assessment of a fluid system includes a scaffold housing with a plurality of internal cavities; a debris monitor module assembly to be selectively inserted into a first cavity of the plurality of internal cavities, the debris monitor module assembly to determine wear debris information in a lubricant; a lubricant condition monitor module assembly to be selectively inserted into a second cavity of the plurality of internal cavities, the lubricant condition monitor module assembly to determine lubricant condition information in the lubricant; and a processing module assembly that is configured to be selectively inserted into a third cavity of the plurality of internal cavities, the processing module assembly to provide communication to an external interface of at least one of the wear debris information and the lubricant condition information.

In addition to one or more of the features described above, or as an alternative, further embodiments could include an electrical connector to receive signals from each of the debris monitor module assembly, the lubricant condition monitor module assembly, and the processing module assembly.

In addition to one or more of the features described above, or as an alternative, further embodiments could include wherein the debris monitor module assembly includes a transducer being electrically coupled to a debris controller.

In addition to one or more of the features described above, or as an alternative, further embodiments could include wherein the transducer obtains the wear debris information, the transducer comprising one or more of an inductive coil, an optical sensing element, a magnetic sensing element and an acoustical sensing element.

In addition to one or more of the features described above, or as an alternative, further embodiments could include wherein each of the debris monitor module assembly, the lubricant condition monitor module assembly, and the processing module assembly are configured to be assembled external to the scaffold housing prior to being selectively coupled to the scaffold housing.

In addition to one or more of the features described above, or as an alternative, further embodiments could include wherein the scaffold housing has an end to receive a lubricant filter.

In addition to one or more of the features described above, or as an alternative, further embodiments could include, wherein the processing module assembly is configured to provide communication to the external interface of both the wear debris information and the lubricant condition information.

In addition to one or more of the features described above, or as an alternative, further embodiments could include, wherein the debris monitor module assembly and the lubricant condition monitor module assembly are positioned in at least one of an in-line flow path, an on-line flow path and an off-line flow path of the lubricant.

According to an aspect of the invention, a method of assembling an apparatus for assessment of a fluid system includes obtaining a scaffold housing with a plurality of internal cavities; placing a debris monitor module assembly into a first cavity of the plurality of internal cavities, the debris monitor module assembly to determine wear debris information in a lubricant; placing a lubricant condition monitor module assembly into a second cavity of the plurality of internal cavities, the lubricant condition monitor module assembly to determine lubricant condition information in the lubricant; and placing a processing module assembly into a third cavity of the plurality of internal cavities, the processing module assembly to provide communication to an external interface of at least one of the wear debris information and the lubricant condition information.

In addition to one or more of the features described above, or as an alternative, further embodiments could include installing the apparatus for assessment of the fluid system in at least one of an in-line flow path, an on-line flow path and an off-line flow path of the lubricant.

In addition to one or more of the features described above, or as an alternative, further embodiments could include installing the apparatus for assessment of the fluid system in an in-line flow path of the lubricant.

In addition to one or more of the features described above, or as an alternative, further embodiments could include installing a lubricant filter to the scaffold housing.

In addition to one or more of the features described above, or as an alternative, further embodiments could include establishing a connection to an electrical connector on the scaffold housing, the electrical connector to receive signals from each of the debris monitor module assembly, the lubricant condition monitor module assembly, and the processing module assembly.

Technical function that is achieved by the combination of features described above includes a modular packaging system with selectively removable/replaceable sensor module assemblies. Individual module assemblies can be adjusted, repaired, or upgraded independently, as needed and prevents a single failed module assembly in a lubricant condition monitor from rendering the monitor non-functional.

Other aspects, features, and techniques of the invention will become more apparent from the following description taken in conjunction with the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which like elements are numbered alike in the several FIGURES:

DETAILED DESCRIPTION

Figure 1:
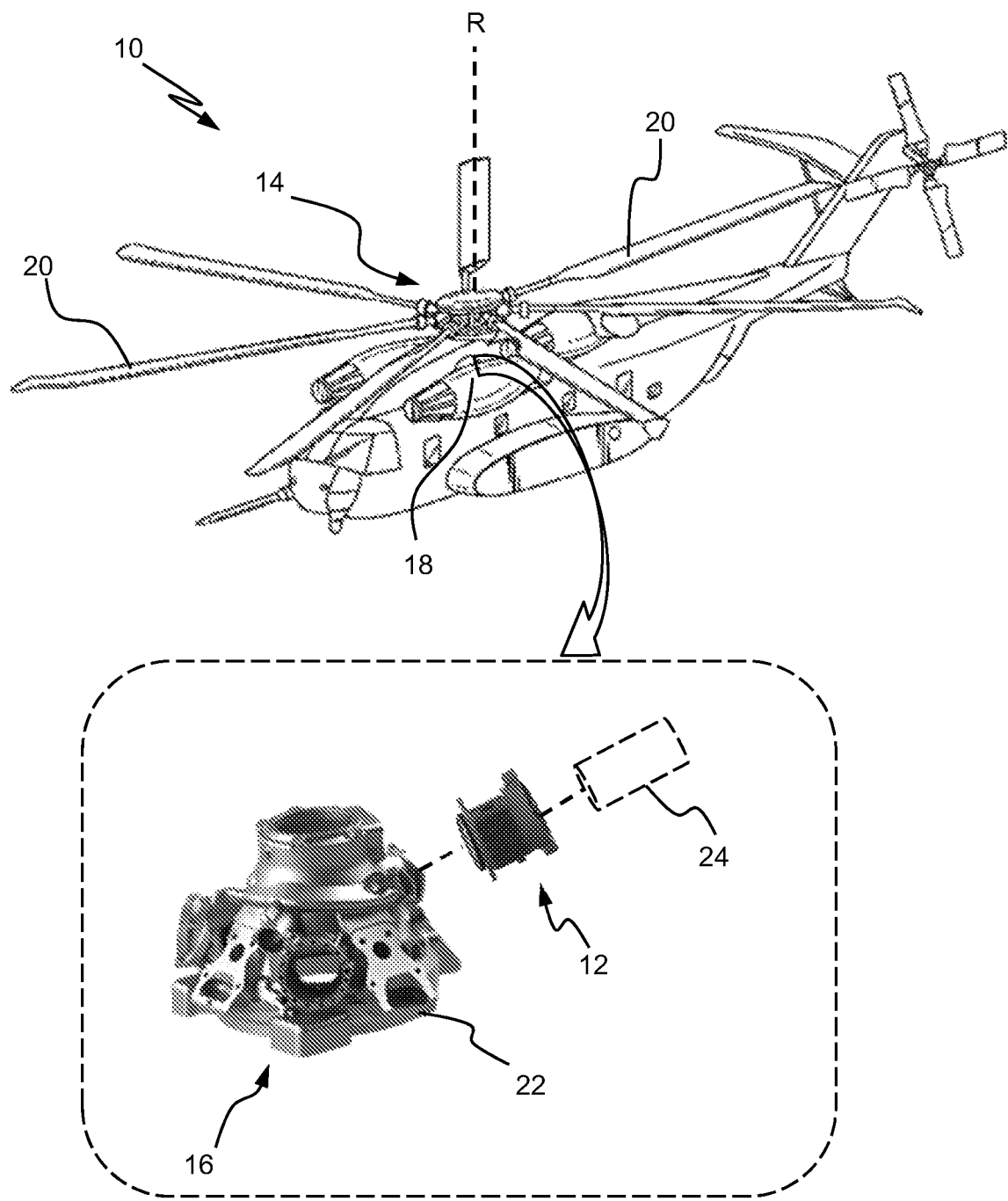
FIG. 1 is a view of an exemplary vehicle for use with a lubricant condition assessment monitor in accordance with an embodiment of the invention.

Referring to the drawings, FIG. 1 illustrates an exemplary vehicle with a gearbox, e.g., a helicopter or aircraft 10 having gearbox 16 with a modular lubricant condition assessment monitor 12 (hereinafter "monitor 12") in accordance with an embodiment of the invention. Monitor 12 is a modular packaging assembly that integrates a plurality of self-contained sensor module assemblies for providing lubrication condition assessment and wear debris detection of a lubricant in gearbox 16. For clarity, lubricant can include oil, or other lubricating fluids. As shown, exemplary aircraft 10 includes main rotor assembly 14 that is driven about an axis of rotation R by one or more engines 18. Main rotor assembly 14 includes a multiple of rotor blades 20 mounted to rotor assembly 14 and are driven for rotation about axis R through a main gearbox 16. Monitor 12 can be embedded as an in-line, on-line or off-line sensor that integrates both lubricant condition monitoring and wear debris detection and particle capture within a modular package with a plurality of sensor module assemblies. Monitor 12 can be positioned in-line with lubricant flow through main gearbox 16 and can be selectively coupled to housing 22 of main gearbox 16. An optional filter 24 can also be provided for removing wear debris from the lubricant as it flows from monitor 12 through filter 24 and back to gearbox 16. While monitor 12 is shown and described being used with a gearbox 16 of aircraft 10, monitor 12 may be used in a variety of applications where lubricant monitoring is desired.

Figure 2A:
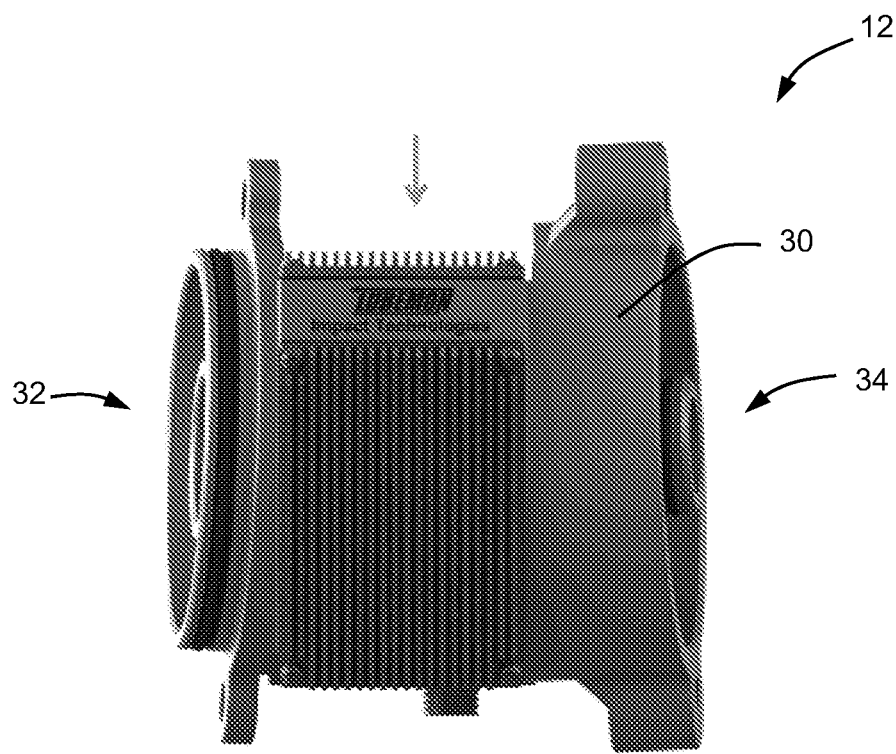
FIG. 2A illustrates a perspective elevation view of the lubricant condition assessment monitor of FIG. 1 in accordance with an embodiment of the invention.
Figure 2B:
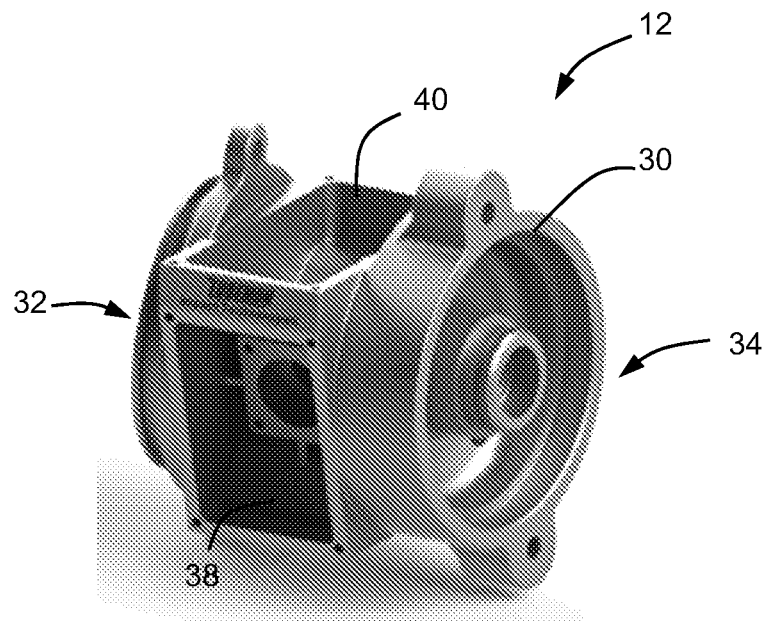
FIG. 2B illustrates a perspective view of a scaffold housing of the lubricant condition assessment monitor of FIG. 1 in accordance with an embodiment of the invention.

FIGS. 2A-2D depict an exemplary embodiment of monitor 12 that is used on a gearbox of a vehicle, e.g., on a main gearbox 16 of aircraft 10 in accordance with an embodiment of the invention. As shown in FIGS. 2A and 2B, monitor 12 includes scaffold housing 30 of unitary construction that can be cast from a metal or a metal alloy. Housing 30 includes a first end 32 that is adapted or configured to be coupled to gearbox 16 and a second end 34 that is adapted or configured to be coupled to an external gearbox filter 24. Housing 30 includes a plurality of internal cavities 38, 40 (shown in FIG. 2B), and 36 (shown in FIG. 2C) that are configured to receive radially mounted sensor module assemblies. Additionally, housing 30 includes one or more pathways that direct lubricant to one or more of the radially mounted sensor module assemblies for detection of wear debris and lubricant condition assessment. The radially mounted sensor module assemblies are configured to provide a sensing solution for lubrication condition assessment and wear debris detection of ferrous and non-ferrous materials in the lubricant as it flows through housing 30.

Figure 2C:
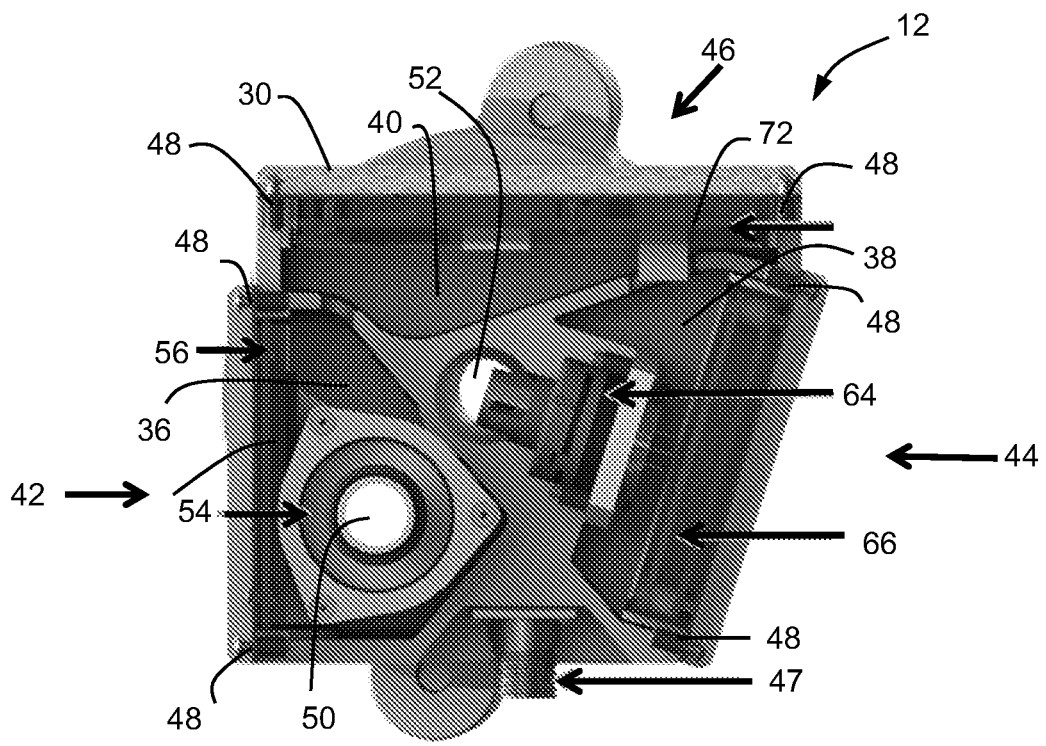
FIG. 2C illustrates a cross-sectional view of the lubricant condition assessment monitor of FIG. 1 in accordance with an embodiment of the invention.
Figure 2D:
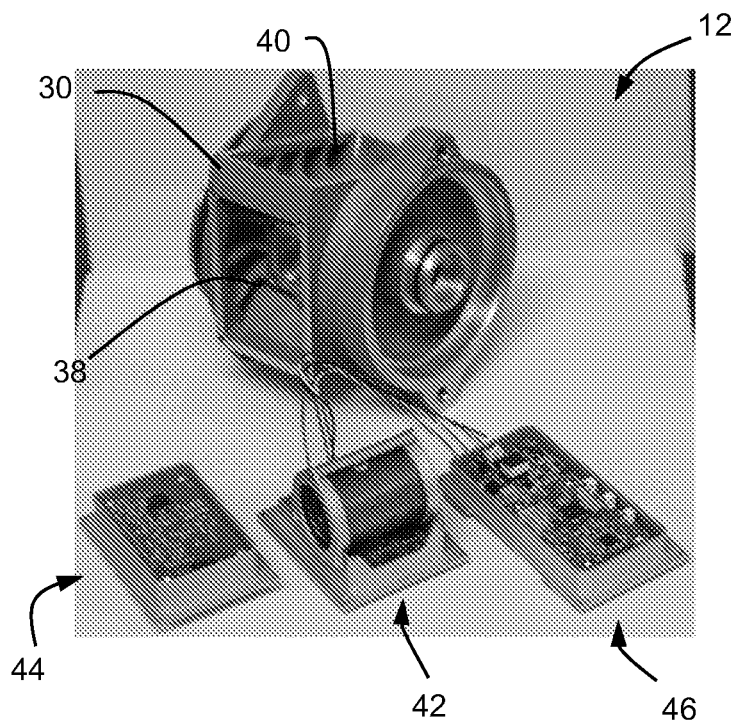
FIG. 2D illustrates a perspective view of a disassembled lubricant condition assessment monitor that is shown with its sensor module assemblies in accordance with an embodiment of the invention.

As shown in FIGS. 2C and 2D, housing 30 includes a plurality of internal cavities 36, 38, and 40 that are configured to receive the radially mounted sensor module assemblies. For example, internal cavity 36 is configured to receive debris monitor module assembly 42; internal cavity 38 is configured to receive lubricant condition monitor module assembly 44; and internal cavity 40 is configured to receive digital processing module assembly 46 (hereinafter "module assemblies 42, 44, and 46"). Each module assembly 42, 44, and 46 is a stand-alone module assembly that is configured to be assembled externally from housing 30. For example, each representative module assembly 42, 44, 46 is configured to be assembled externally to housing 30 with its components and circuit boards encapsulated in a thermally conductive potting compound and be selectively inserted into respective internal cavities 36, 38, and 40 in order to replace a defective module assembly or upgrade a module assembly. In an embodiment, each module assembly 42, 44, and 46 is coupled to housing 30 through a plurality of fasteners 48. Module assemblies 42, 44, and 46 are in electrical communication with an electrical connector 47, for example, a D38999 mil-std connector. Housing 30 includes a pathway 50 that is configured to direct lubricant through debris monitor module assembly 42 and pathway 52 that is configured to direct lubricant through housing 30 for assessment by lubricant condition monitor module assembly 44. A benefit of providing an encapsulated module assembly over conventional housings is a reduction in weight of the monitor 12 by providing thermal potting compound in individual standalone module assemblies in lieu of thermal potting compound in substantially the entire cavity of conventional housings.

Figure 3:
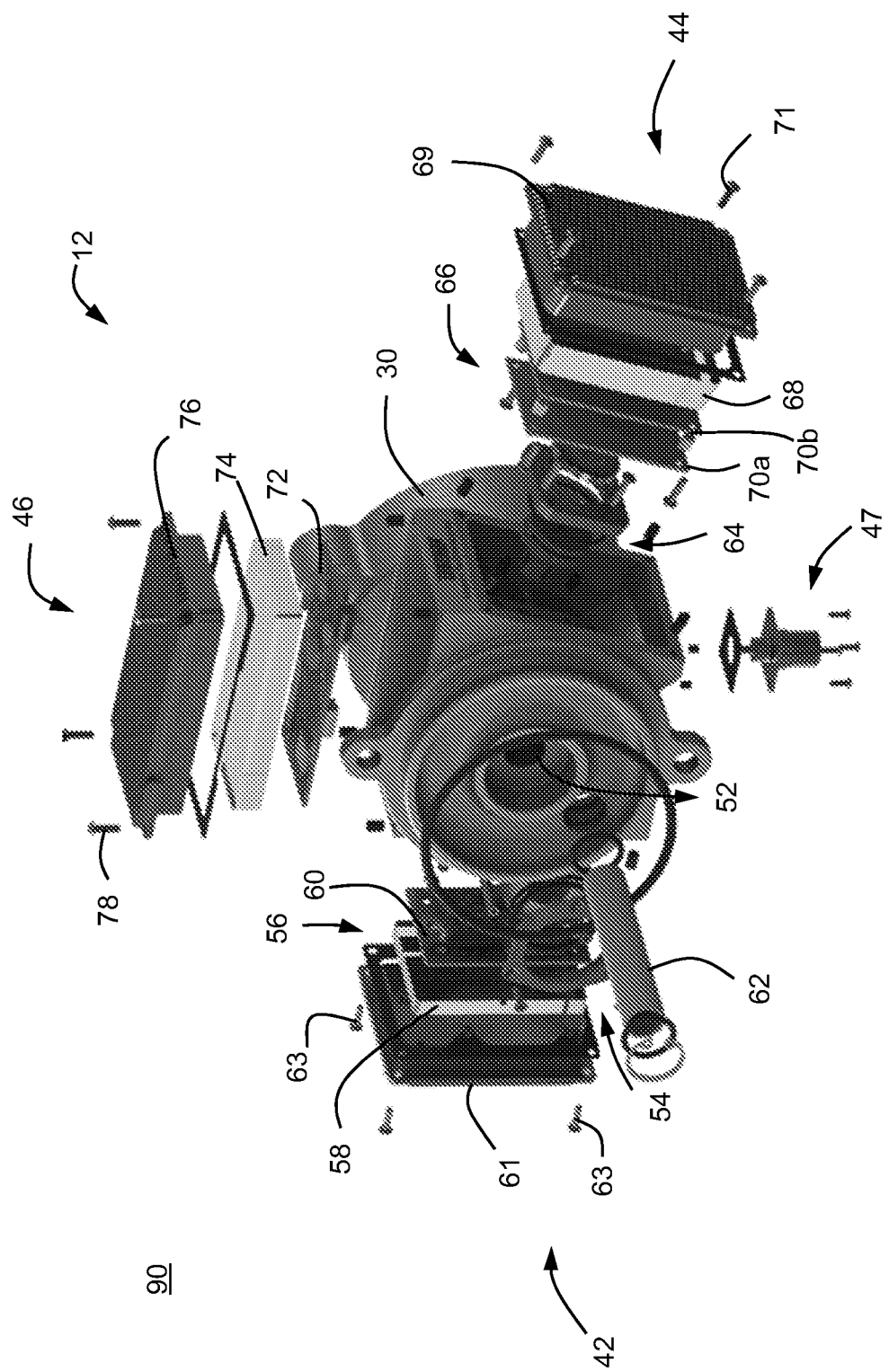
FIG. 3 depicts an exploded view of the lubricant condition assessment monitor in accordance with an embodiment of the invention.

Referring to FIG. 3 with continued reference to FIG. 2C, monitor 12 includes the plurality of module assemblies 42, 44, and 46 that are pre-assembled externally and later inserted into housing 30 to replace or upgrade a respective module assembly. Debris monitor module assembly 42 includes a transducer 54 that is in communication with a debris controller 56. An exemplary transducer 54 is an inductive coil that creates a magnetic field when excited by a high frequency alternating current. The inductive coil detects wear debris particles in the lubricant by detecting the interaction between particles and the inductive coil. Transducer 54 may be implemented using one or more of an inductive coil, an optical sensing element, magnetic sensing element, acoustical sensing element, etc.

Debris monitor module assembly 42 is pre-assembled with a transducer 54 and debris controller 56. Debris monitor module assembly 42 can be assembled external to housing 30 and subsequently inserted into housing 30 as a standalone module assembly. Debris controller 56 includes components that are assembled on circuit board 60 and encapsulated in a thermal potting compound 58 to form a sub-assembly. The sub-assembly is coupled to transducer 54 during final assembly to form debris monitor module assembly 42. Transducer 54 is configured to be "wetted" by lubricant (i.e., in contact with lubricant) after insertion of module assembly 42 into housing 30. An external cover 61 can be inserted over the assembly after coupling to housing 30 and held in place with screws 63. In an embodiment, the external surface of cover 61 can include fins to provide passive cooling by transferring heat from module assembly 42 through thermal potting compound 58 to the external environment 90. Further, debris monitor module assembly 42 is configured to receive a polyether ether ketone (PEEK) tube 62 that provides pathway 50 for flow of lubricant through module assembly 42. Debris controller 56 generates electric and magnetic fields in an inductive coil and includes a phase-sensitive demodulator for detecting real and imaginary impedance shifts in the magnetic and electric field lines caused by ferrous or non-ferrous wear debris particles in lubricant as it flows through pathway 50. Debris controller 56 may be implemented as a microcontroller, DSP, microprocessor or similar device and includes a memory. The memory may store a debris detection algorithm as executable instructions for identifying ferrous and non-ferrous wear debris particles and count of wear debris particles in the lubricant.

Similarly, lubricant condition monitor module assembly 44 is pre-assembled with a transducer 64 and lubricant condition controller 66 prior to insertion into housing 30. Lubricant condition monitor module assembly 44 can be assembled external to housing 30 and subsequently be inserted into housing 30 as a standalone module assembly. Lubricant condition controller 66 includes components that are assembled on circuit boards 70a and 70b and encapsulated in a thermal potting compound 68 to form a sub-assembly. The sub-assembly is coupled to transducer 64 during final assembly to form lubricant condition monitor module assembly 44. An external cover 69 can be inserted over the assembly after coupling to housing 30 and held in place with screws 71. In an embodiment, the external surface of cover 69 can include fins to provide passive cooling by transferring heat from module assembly 44 through thermal potting compound 68 to the external environment 90. Lubricant condition monitor module assembly 44 performs oil condition assessment of lubricant in main gearbox 16 through transducer 64 in order to detect and classify lubricant quality factors such as water content, incorrect lubricant addition, lubricant oxidation degradation, additive depletion, or the like. In an embodiment, lubricant condition monitor module assembly 44 can perform lubricant condition assessment of "filtered" lubricant that is received from gearbox filter 24 (shown in FIG. 1) as it exits gearbox filter 24 and traverses back through housing 30 through pathway 52. The lubricant condition monitor module assembly 44 uses transducer 64 to measure changes in the electrochemical response of the lubricant and estimates the change in specific aspects of lubricant health through a lubricity impedance model. The lubricant condition monitor module assembly 44 injects a broadband AC voltage signal into the lubricant and measures the response at the frequency of the injected signal. The impedance of the lubricant can then be determined by comparing the differences between the injected signal and the response signal. Lubrication condition controller 66 generates injection signals and processes the received signals for impedance. Lubricant condition controller 66 may be implemented as a microcontroller, DSP, microprocessor or similar device and includes a memory. The memory may store a lubricant quality algorithm as executable instructions and models for interrogation and analysis of the received signal in order to detect and classify lubricant quality factors in the lubricant. Exemplary lubricant quality factors include water content, incorrect lubricant addition, lubricant oxidation degradation, or additive depletion. Also, lubricant condition controller 66 may communicate information through a digital communications interface to digital processing module assembly 46 for signal processing and communication.

Further, digital processing module assembly 46 is pre-assembled and can be subsequently inserted into housing 30 as a standalone module assembly. Digital processing module assembly 46 includes components that are assembled onto communication controller board 72 and encapsulated in a thermal potting compound 74. An external cover 76 can be inserted over the assembly after coupling to housing 30 and held in place with screws 78. In an embodiment, the external surface of cover 76 can include fins to provide passive cooling by transferring heat from module assembly 46 through thermal potting compound 74 to the external environment 90. Digital processing module assembly 46 can include a CAN-J1939 or RS-485/232 Modbus communications for high-level digital communication with debris monitor module assembly 42 and lubricant condition monitor module assembly 44 as well as diagnostic and prognostic algorithms for processing and analyzing information that is received from debris monitor module assembly 42 and lubricant condition monitor module assembly 44 and providing on-line communications for prognostics and health monitoring ("PHM"). Data communication includes receiving data signals related to wear debris detection and lubricant condition assessment from module assemblies 42 and 44, respectively. Communication controller board 72 includes on-board signal processing and analysis of received data signals from module assemblies 42 and 44 and can include one or more algorithms for PHM as well as communicating the processed information on-line to external interfaces through electrical connector 47. In an embodiment, communication controller board 72 can process digital data received from module assemblies 42 and 44, and provide this information to an external interface upon interrogation of communication controller board 72.

Figure 4:
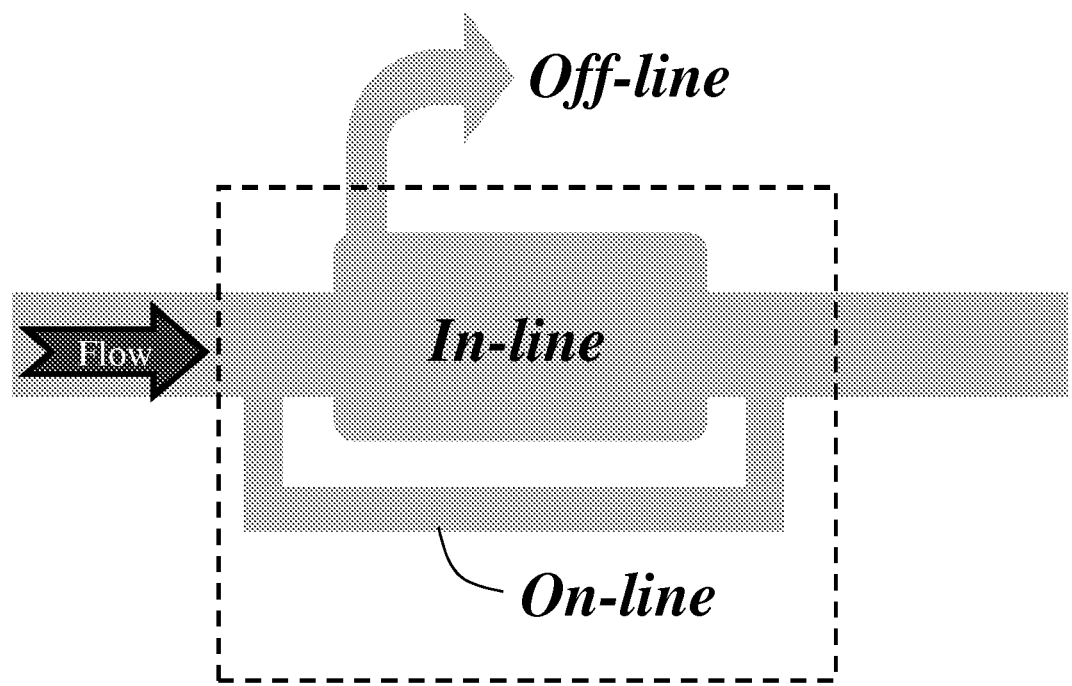
FIG. 4 depicts exemplary lubricant condition assessment topologies for use with the lubricant condition assessment monitor.

As shown in FIG. 1, monitor 12 may be used in an in-line configuration, where the monitor 12 is installed in a fluid flow path from gearbox 22 to filter 24. Monitor 12 may also be used in on-line or off-line configurations. FIG. 4 depicts exemplary topologies for use with monitor 12. In one topology, referred to as an in-line flow path, all lubricant from the gearbox 22 passes through the monitor 12 for inspection, to filter 24, and is then returned to gearbox 22. In an alternate topology, referred to as an on-line flow path, a portion of the lubricant is diverted from the full flow path, passes through the monitor 12, and then returns to the full flow path. This on-line flow path topology may be implemented as part of a "kidney loop" which includes additional filtering of the lubricant. In an alternate topology, referred to as an off-line flow path, lubricant is removed from the system and passed through the monitor 12 for analysis, for example at a test station. The off-line flow path may also be part of a "kidney loop" which includes additional filtering of the lubricant.

Benefits that are achieved by embodiments described herein include a modular packaging system with selectively removable/replaceable sensor module assemblies that prevents a single failed module assembly in a lubricant condition monitor from rendering the monitor non-functional. Individual module assemblies can be adjusted, repaired, or upgraded independently, as needed. The volume and associated weight of thermal potting compound required to protect components from vibration can be more easily minimized. Use of individual module assemblies can also reduce the cost and complexity of manufacturing the lubricant condition assessment monitor as a whole by moving many of each sensor module assemblies' precision tolerances into smaller, more dimensionally manageable subassemblies. Embodiments also reduce non-recurring engineering necessary to adapt the monitor to different platforms as only the scaffold housing needs redesign to work in other applications.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. Many modifications, variations, alterations, substitutions or equivalent arrangements not hereto described will be apparent to those of ordinary skill in the art without departing from the scope and spirit of the invention. Additionally, while the various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. An apparatus for assessment of a fluid system, comprising:
   a scaffold housing with a plurality of cavities;
   a debris monitor module assembly to be selectively inserted into a first cavity of the plurality of cavities, the debris monitor module assembly to determine wear debris information in a lubricant;
   a lubricant condition monitor module assembly to be selectively inserted into a second cavity of the plurality of cavities, the lubricant condition monitor module assembly to determine lubricant condition information in the lubricant; and
   a processing module assembly that is configured to be selectively inserted into a third cavity of the plurality of cavities, the processing module assembly to provide communication to an external interface of at least one of the wear debris information and the lubricant condition information,
   wherein each module assembly is arranged on the scaffold housing to be insertable on and removable from a respective cavity of the plurality of cavities of the scaffold housing.

2. The apparatus of claim 1, further comprising an electrical connector to receive signals from each of the debris monitor module assembly, the lubricant condition monitor module assembly, and the processing module assembly.

3. The apparatus of claim 1, wherein the debris monitor module assembly includes a transducer being electrically coupled to a debris controller.

4. The apparatus of claim 3, wherein the transducer obtains the wear debris information, the transducer comprising one or more of an inductive coil, an optical sensing element, a magnetic sensing element and an acoustical sensing element.

5. The apparatus of claim 1, wherein each of the debris monitor module assembly, the lubricant condition monitor module assembly, and the processing module assembly are configured to be assembled external to the scaffold housing prior to being selectively coupled to the scaffold housing.

6. The apparatus of claim 1, wherein the scaffold housing has an end to receive a lubricant filter.

7. The apparatus of claim 1, wherein the processing module assembly is configured to provide communication to the external interface of both the wear debris information and the lubricant condition information.

8. The apparatus of claim 1, wherein the debris monitor module assembly and the lubricant condition monitor module assembly are positioned in at least one of an in-line flow path, an on-line flow path and an off-line flow path of the lubricant.

9. A method of assembling an apparatus for assessment of a fluid system, the method comprising:
   obtaining a scaffold housing with a plurality of cavities;
   placing a debris monitor module assembly into a first cavity of the plurality of cavities, the debris monitor module assembly to determine wear debris information in a lubricant;
   placing a lubricant condition monitor module assembly into a second cavity of the plurality of cavities, the lubricant condition monitor module assembly to determine lubricant condition information in the lubricant; and placing a processing module assembly into a third cavity of the plurality of cavities, the processing module assembly to provide communication to an external interface of at least one of the wear debris information and the lubricant condition information, wherein each module assembly is arranged on the scaffold housing to be insertable on and removable from a respective cavity of the plurality of cavities of the scaffold housing.

10. The method of claim 9 further comprising installing the apparatus for assessment of the fluid system in at least one of an in-line flow path, an on-line flow path and an off-line flow path of the lubricant.

11. The method of claim 9 further comprising installing the apparatus for assessment of the fluid system in an in-line flow path of the lubricant.

12. The method of claim 9 further comprising installing a lubricant filter to the scaffold housing.

13. The method of claim 9, further comprising establishing a connection to an electrical connector on the scaffold housing, the electrical connector to receive signals from each of the debris monitor module assembly, the lubricant condition monitor module assembly, and the processing module assembly.

14. The system of claim 1, wherein components of the debris monitor module assembly, components of the lubricant condition monitor module assembly, and components of the processing module assembly are each encapsulated by a respective portion of a potting compound.

15. The method of claim 9 further comprising:
encapsulating components of the debris monitor module assembly, components of the lubricant condition monitor module assembly, and components of the processing module assembly in a respective portion of a potting compound.

16. The system of claim 1, wherein the scaffold housing comprises a first face comprising the first cavity, a second face comprising the second cavity, and a third face comprising the third cavity, wherein the third face is connected to the first face at a first edge portion, and wherein the third face is connected to the second face at a second edge portion.

* * * * *